(12) United States Patent
Falco et al.

(10) Patent No.: US 6,627,798 B2
(45) Date of Patent: Sep. 30, 2003

(54) AROMATIC AMINO ACID BIOSYNTHETIC ENZYMES

(75) Inventors: Saverio Carl Falco, Arden, DE (US); Omolayo O. Famodu, Newark, DE (US); Jian-Ming Lee, West Caldwell, NJ (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/454,279

(22) Filed: Dec. 3, 1999

(65) Prior Publication Data

US 2002/0184658 A1 Dec. 5, 2002

Related U.S. Application Data

(60) Provisional application No. 60/110,845, filed on Dec. 4, 1998.

(51) Int. Cl.$^7$ .......................... A01H 1/00; C07H 21/04; C07K 14/415; C12N 5/14; C12N 9/00
(52) U.S. Cl. ..................... 800/298; 435/69.1; 435/183; 435/410; 435/419; 435/252.3; 435/320.1; 530/350; 530/370; 536/23.6; 536/24.1; 536/24.33; 800/295
(58) Field of Search ................................ 435/183, 410, 435/419, 252.3, 320.1; 530/350, 370; 536/23.6, 24.1, 24.33; 800/278, 295

(56) References Cited

PUBLICATIONS

Bork, P. Genome Research, vol. 10, p. 398–400, 2000.*
Dinesh Christendat et al., Biochemistry, vol. 35:4468–4479, Identification of Active Site Residues of Chorismate Mutase—Prephenate Dehydrogenase from *Escherichia coli*, 1996.
Singh et al., (1985) Arch. Biochem. Biophys. 243:374–384.
NCBI General Identifier No. 1168940.
FEBS Lett., 334(2):233–236 (1993) Eberhard et al.
NCBI General Identifier No. 5732016.
Plant J. 10(5):815–821 (1996) Eberhard et al.
NCBI General Identifier No. 3184059.
NCBI General Identifier No. 6319643.
EMBO J. 13(24):5795–5809 (1994) Feldmann et al.
Science 274(5287):546 (1996) Goffeau et al.
Cotton and Gibson (1968) Biochim. Biophys. Acta 156:187–189.
Fischer and Jensen (1987) Methods Enzymol. 142:503–507.

* cited by examiner

*Primary Examiner*—Phuong T. Bui

(57) ABSTRACT

This invention relates to an isolated nucleic acid fragment encoding a tyrosine biosynthetic enzyme. The invention also relates to the construction of a chimeric gene encoding all or a portion of the tyrosine biosynthetic enzyme, in sense or antisense orientation, wherein expression of the chimeric gene results in production of altered levels of the tyrosine biosynthetic enzyme in a transformed host cell.

14 Claims, 2 Drawing Sheets

```
SEQ ID NO:21    MRSSCCSSAIGGFFDHRRELSTSTPISTLLPLPSTKSSFSVRCSLPQPSKPRSGTSSVHA
SEQ ID NO:12    ------------------------------------------PAPRNKG-----LRAANNSATPIAKVE-
SEQ ID NO:14    ----------------------------------------------K----------------Q--
SEQ ID NO:22    MARVFESDSGSG------------------------------------------------
SEQ ID NO:16    MAKAAEQSPDSG----------------------------------CS------------
SEQ ID NO:18    ------------------------------------------------------------
                1                                                          60

SEQ ID NO:21    VMTLAGSLTGKKRVDESESLTLEGIRNSLIRQEDSIIFGLLERAKYCYNADTYDPTAF-D
SEQ ID NO:12    -------RVDRSDILTLDSIRQVLIRLEDSIIFGLLERAQFCYNADTYDSNAF-H
SEQ ID NO:14    -------RIDQSEILTLDNIRTSLVRQEDSIIFSLLERAQFCYNADIYDKNAF-H
SEQ ID NO:22    ----------NVLSLDLIRESLIRQEDTIVFSLIERAKFPLNSPAFEESRCLD
SEQ ID NO:16    ----------NVYTLASVREDLVRQEDTIIYGLIERAKFPSNSHTYDE-KYAQ
SEQ ID NO:18    ------------------------------------------------------------
                61                                                        120

SEQ ID NO:21    *   **         *            *         *    **     *
                MDGFNGSLVEYMVKGTEKLHAKVGRFKSPDEHPFFPDDLPEPMLPPLQYPKVLHFEAADSI
SEQ ID NO:12    MDGFGGSLVEYIVRETEKLHAQVGRYKSPDEHPFFSKDLPEPRLPPMQYPRVLHPIADSI
SEQ ID NO:14    VDGFDGSLVEFMVRETEKLHQQVGRYKSPDEHPFFPEDLPEPLLPPLQYPKVLHPIADSI
SEQ ID NO:22    SGSF-SSLTEFVRETEIIQAKVGRYEYPEENPFFLENIPHSVFPTHKYPSALHPKALSV
SEQ ID NO:16    IQGFCGSLVEFVVKNTEAIQAKAGRYKNPEENAFFPENLPPSIVPSYSFKQFLHPGAASI
SEQ ID NO:18    ------ARAEFFVREAEVLHAKAGHYQKPEDVPFFSQDLPPPVFPTKGRPKVLHPFASLV
                121                                                       180
```

FIG. 1A

```
                              *       *  ***  **   *   *   **   * *** ** ***  *
SEQ ID NO:21    NINKKIWNMYFRDLVPRLVKKGDDGNYGSTAVCDAICLQCLSKRIHYGKFVAEAKFQASP
SEQ ID NO:12    NINKEIWKMYFDELLPRLVKEGSDGNAGSSALCDTTCLQALSRRIHYGKFVAEAKFQESP
SEQ ID NO:14    NINKEIWKMYFDELLPRLVKEGSDGNYGSSALCDTICLQALSKRIHYGKFVAEAKFQESP
SEQ ID NO:22    NINKQIWDIYFKELLPLFVKPGDDGNYPSTAASDLACIQALSRRIHYGKFVAEVKFRDAP
SEQ ID NO:16    NINKSIWKMYFKELLPLLATSGDDGNYAQTAANDLSLLQSISRRIHYGKFVAEVKFRDAP
SEQ ID NO:18    CVNDAIWKMYFNELLPLFTADGDDGNYAETVALDFACLQALSRRIHCGKYVAEVKFKDAP
                181                                                        240

*    *     **    * **        *   **       ** * *
SEQ ID NO:21    EAYESAIKAQDKDRLMDMLTFPTVEDAIKKRVEMKTRTYGQEVKVGMEEKEEEEGNES
SEQ ID NO:12    EAYTPAIIAQDRDQLMNLLTYETVERAIEHRVEAKAKIFGQEVNIG------AKDNGSP
SEQ ID NO:14    EAYMPAIIAQDCDQLMHLLTYETVERAIEHRVEAKAKIFGQEVDLG------AEDNGAP
SEQ ID NO:22    QDYEPAIRAQDREALMKLLTFEKVEEMVKKRVQKKAETFGQEVKF--NSGYGDES----K
SEQ ID NO:16    QDYEPLIRAKDKEGLMKLLTFTSVEETVRKRVEKKAVVFGQEVNL--NSDDNDNE----N
SEQ ID NO:18    QDYSPPIRAKDTNALMNLLTFTAVEEKVKKRVEKKARIFGQNVTL--EDSVGKQDGDACD
                241                                                        300

*                  *  **   *  ********
SEQ ID NO:21    HVYKISPILVGDLYGDWIMPLTKEVQVEYLLRRLD
SEQ ID NO:12    PVYKIRPSLVAELYSYRIMPLTKEVEVAYLLKRLD
SEQ ID NO:14    PMYKIRPSLVAELYSYRIMPLTKEVQVAYLLRRLD
SEQ ID NO:22    KKYKVDPLLASRIYGEWLIPLTKLVEVEYLLRRLD
SEQ ID NO:16    RKF--DPSVASSLYKNWVIPLTKEVQVEYLLRRLD
SEQ ID NO:18    SHCKVDPKVLSKLYDMWVMPLTKDVEVEYLLRRLD
                301                                335
```

FIG. 1B

AROMATIC AMINO ACID BIOSYNTHETIC ENZYMES

This application claims priority benefit of U.S. Provisional Application No. 60/110,845 filed Dec. 4, 1998, now pending.

FIELD OF THE INVENTION

This invention is in the field of plant molecular biology. More specifically, this invention pertains to nucleic acid fragments encoding tyrosine biosynthetic enzymes in plants and seeds.

BACKGROUND OF THE INVENTION

Animals do not synthesize aromatic amino acids so it is necessary to include them in their diets. In the aromatic amino acid biosynthetic pathway chorismate is converted to anthranilate during tryptophan biosynthesis and it is converted to prephenate, the branch point for tyrosine and phenylalanine biosynthesis. Chorismate mutase catalyzes the conversion of chorismate to prephenate. Two different isoforms of chorismate mutase have been identified. A chorismate mutase located in the chloroplasts (CM-1) is activated by tryptophan and inhibited by phenylalanine and tyrosine while a cytoplasmic chorismate mutase (CM-2) is insensitive to the presence of all three aromatic amino acids (Singh et al. (1985) *Arch. Biochem. Biophys.* 243:374–384).

Prephenic acid is converted to tyrosine either by a) oxidative decarboxylation catalyzed by prephenate dehydrogenase followed by transamination catalyzed by aromatic aminotransferase or by b) transamination of prephenate catalyzed by prephenate aminotransferase followed by oxidative decarboxylation catalyzed by arogenate dehydrogenase. Arogenate dehydrogenase activity is commonly found in plants while prephenate dehydrogenase activity has been difficult to detect.

SUMMARY OF THE INVENTION

The present invention relates to isolated polynucleotides comprising a nucleotide sequence encoding a polypeptide of at least 62 amino acids that has at least 80% identity based on the Clustal method of alignment when compared to a polypeptide selected from the group consisting of a corn chorismate mutase polypeptide of SEQ ID NOs:2 and 12, a rice chorismate mutase polypeptide of SEQ ID NOs:4 and 14, a soybean chorismate mutase polypeptide of SEQ ID NOs:6 and 16, a wheat chorismate mutase polypeptide of SEQ ID NOs:8 and 18. The present invention also relates to an isolated polynucleotide comprising the complement of the nucleotide sequences described above.

The present invention relates to isolated polynucleotides comprising a nucleotide sequence encoding a polypeptide of at least 60 amino acids that has at least 80% identity based on the Clustal method of alignment when compared to a polypeptide selected from the group consisting of a soybean prephenate dehydrogenase polypeptide of SEQ ID NOs:10 and 20. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, and 19 that codes for the polypeptide selected from the group consisting of SEQ ID NOs:2, 4, 6, 8, 10, 12, 14, 16, 18, and 20. The present invention also relates to an isolated polynucleotide comprising a nucleotide sequences of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, and 19 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a chorismate mutase polypeptide of at least 62 amino acids comprising at least 80% homology based on the Clustal method of alignment compared to a polypeptide selected from the group consisting of SEQ ID NOs:2, 4, 6, 8, 12, 14, 16, and 18.

The present invention relates to a prephenate dehydrogenase polypeptide of at least 60 amino acids comprising at least 80% homology based on the Clustal method of alignment compared to a polypeptide selected from the group consisting of SEQ ID NOs:10 and 20.

The present invention relates to a method of selecting an isolated polynucleotide that affects the level of expression of a chorismate mutase or a prephenate dehydrogenase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a chorismate mutase or a prephenate dehydrogenase polypeptide in the host cell containing the isolated polynucleotide; and (d) comparing the level of the chorismate mutase or the prephenate dehydrogenase polypeptide in the host cell containing the isolated polynucleotide with the level of the chorismate mutase or the prephenate dehydrogenase polypeptide in the host cell that does not contain the isolated polynucleotide.

The present invention relates to a method of obtaining a nucleic acid fragment encoding a substantial portion of a chorismate mutase or a prephenate dehydrogenase polypeptide gene, preferably a plant chorismate mutase or prephenate dehydrogenase polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, and 19 and the complement of such nucleotide sequences; and amplifying a nucleic acid fragment (preferably a cDNA inserted in a cloning vector) using the oligonucleotide primer. The amplified nucleic acid fragment preferably will encode a portion of a chorismate mutase or a prephenate dehydrogenase amino acid sequence.

The present invention also relates to a method of obtaining a nucleic acid fragment encoding all or a substantial portion of the amino acid sequence encoding a chorismate mutase or a prephenate dehydrogenase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a horismate mutase or a prephenate dehydrogenase, the method comprising the steps of: (a) transforming a host cell with a chimeric gene comprising a nucleic acid fragment encoding a horismate mutase or a prephenate dehydrogenase, operably linked to suitable regulatory sequences; (b) growing the transformed host cell under conditions that are suitable for expression of the chimeric gene wherein expression of the chimeric gene results in production of chorismate mutase or prephenate dehydrogenase in the transformed host cell; (c) optionally purifying the chorismate mutase or the prephenate dehydrogenase expressed by the transformed host cell; (d) treating the chorismate mutase or the prephenate dehydrogenase with a compound to be tested; and (e) comparing the activity of the chorismate mutase or the prephenate dehydrogenase that has been treated with a test compound to the activity of an untreated chorismate mutase or prephenate dehydrogenase, thereby selecting compounds with potential for inhibitory activity.

The present invention relates to a composition, such as a hybridization mixture, comprising an isolated polynucleotide of the present invention.

The present invention relates to an isolated polynucleotide of the present invention comprising at least 30 contiguous nucleotides derived from a nucleic acid sequence selected from the group consisting of SEQ ID NOs:1, 3, 5, 7, 9, 11, 13, 15, 17, and 19.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the tyrosine biosynthetic enzyme polynucleotide in an amount sufficient to complement a null mutant to provide a positive selection means.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A–1B show a comparison of the amino acid sequences of the chorismate mutase from corn clone cen1.pk0081.a3:fis (SEQ ID NO:12), rice clone rls48.pk0012.d4:fis (SEQ ID NO:14), soybean clone src1c.pk001.e2:fis (SEQ ID NO:16), wheat clone wr1.pk0081.a8:fis (SEQ ID NO:18), *Arabidopsis thaliana* set forth in NCBI General Identifier No. 1168940 (SEQ ID NO:21), and *Arabidopsis thaliana* set forth in NCBI General Identifier No. 5732016 (SEQ ID NO:22). Amino acids conserved among all sequences are indicated with an asterisk (*) on the top row; dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Tyrosine Biosynthetic Enzymes

| Protein | Clone Designation | SEQ ID NO: (Nucleotide) | SEQ ID NO: (Amino Acid) |
|---|---|---|---|
| Corn Chorismate Mutase | cen1.pk0081.a3 | 1 | 2 |
| Rice Chorismate Mutase | rls48.pk0012.d4 | 3 | 4 |
| Soybean Chorismate Mutase | src1c.pk001.e2 | 5 | 6 |
| Wheat Chorismate Mutase | Contig of: wr1.pk0081.a8 wr1.pk0026.f10 | 7 | 8 |
| Soybean Prephenate Dehydrogenase | sls2c.pk004.f4 | 9 | 10 |
| Corn Chorismate Mutase | cen1.pk0081.a3:fis | 11 | 12 |
| Rice Chorismate Mutase | rls48.pk0012.d4:fis | 13 | 14 |
| Soybean Chorismate Mutase | src1c.pk001.e2:fis | 15 | 16 |
| Wheat Chorismate Mutase | wr1.pk0081.a8:fis | 17 | 18 |
| Soybean Prephenate Dehydrogenase | sls2c.pk004.f4:fis | 19 | 20 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOs:1, 3, 5, 7, 9, 11, 13, 15, 17, 19, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19 and the complement of such nucleotide sequences may be used in methods of selecting an isolated polynucleotide that affects the expression of a polypeptide (such as a chorismate mutase or a prephenate dehydrogenase) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6X SSC, 0.5% SDS at room temperature for 15 min, then repeated with 2X SSC, 0.5% SDS at 45° C. for 30 min, and then repeated twice with 0.2X SSC, 0.5% SDS at 50° C. for 30 min. A more preferred set of stringent conditions uses higher temperatures in which the washes are identical to those above except for the temperature of the final two 30 min washes in 0.2X SSC, 0.5% SDS was increased to 60° C. Another preferred set of highly stringent conditions uses two final washes in 0.1X SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUYLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. "Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several tyrosine biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other chorismate mutases or prephenate dehydrogenases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems.

In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) Proc. Natl. Acad. Sci. USA 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as a chorismate mutase or a prephenate dehydrogenase) preferably a substantial portion of a plant polypeptide of a gene, comprising the steps of: synthesizing an oligonucleotide primer comprising a nucleotide sequence of at least one of 60 (preferably at least 40, most preferably at leas 30) contiguous nucleotides derived from a nucleotide sequence selected from the group consisting of SEQ ID NOs:1, 3, 5, 7, 9, 11, 13, 15, 17, 19, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (such as a chorismate mutase or a prephenate dehydrogenase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of aromatic amino acids in those cells. Because aromatic amino acids are synthesized only in plants and microorganisms chorismate mutase and prephenate dehydrogenase are good targets for herbicides that will not affect animals. Overexpression of these enzymes may also be useful to increase the content of aromatic amino acids in food crops.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded tyrosine biosynthetic enzyme. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in tyrosine biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---------|--------|-------|
| cen1 | Corn Endosperm 10 to 11 Days After Pollination | cen1.pk0081.a3 |
| rls48 | Rice Leaf 15 Days After Germination, 48 Hours After Infection of Strain *Magaporthe grisea* 4360-R-67 (AVR2-YAMO); Susceptible | rls48.pk0012.d4 |
| sls2c | Soybean Infected With *Sclerotinia sclerotiorum* Mycelium | sls2c.pk004.f4 |
| src1c | Soybean 8 Day Old Root Infected With Cyst Nematode | src1c.pk001.e2 |
| wr1 | Wheat Root From 7 Day Old Seedling | wr1.pk0026.f10 |
| wr1 | Wheat Root From 7 Day Old Seedling | wr1.pk0081.a8 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding tyrosine biosynthetic enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Chorismate Mutase

The BLASTX search using the EST sequences from clones listed in Table 3 revealed similarity of the polypeptides encoded by the cDNAs to chorismate mutase from *Arabidopsis thaliana* (NCBI General Identifier No. 1168940). Shown in Table 3 are the BLAST results for individual ESTs ("EST"), or contigs assembled from two or more ESTs ("Contig"):

TABLE 3

BLAST Results for Sequences Encoding Polypeptides
Homologous to Chorismate Mutase

| Clone | Status | BLAST pLog Score 1168940 |
|---|---|---|
| cen1.pk0081.a3 | EST | 20.30 |
| rls48.pk0012.d4 | EST | 19.00 |
| src1c.pk001.e2 | EST | 40.15 |
| Contig of:<br>wr1.pk0081.a8<br>wr1.k0026.f10 | Contig | 47.30 |

The sequence of the entire cDNA insert in the most 5' clones mentioned above was determined and the BLASTP search using the nucleotide sequences from clones listed in Table 4 revealed similarity of the polypeptides encoded by the cDNAs to chorismate mutases from *Arabidopsis thaliana* (General Identifier Nos. 1168940 and 5732016, respectively). Shown in Table 4 are the BLAST results the sequences of the entire cDNA inserts comprising the indicated cDNA clones ("FIS"), or sequences encoding the entire protein derived from an FIS ("CGS"):

TABLE 4

BLAST Results for Sequences Encoding Polypeptides
Homologous to Chorismate Mutases

| | | BLAST pLog Score | |
|---|---|---|---|
| Clone | Status | 1168940 | 5732016 |
| cen1.pk0081.a3:fis | CGS | 98.40 | 68.30 |
| rls48.pk0012.d4:fis | FIS | 102.00 | 69.00 |
| src1c.pk001.e2:fis | CGS | 72.00 | 86.40 |
| wr1.pk0081.a8:fis | FIS | 51.00 | 63.40 |

FIGS. 1A–1B present an alignment of the amino acid sequences set forth in SEQ ID NOs:12, 14, 16, and 18 and the *Arabidopsis thaliana* sequences (SEQ ID NOs:21 and 22). The data in Table 5 represents a calculation of the percent identity of the amino acid sequences set forth in SEQ ID NOs:12, 14, 16, and 18 and the *Arabidopsis thaliana* sequences (SEQ ID NOs:21 and 22).

TABLE 5

Percent Identity of Amino Acid Sequences Deduced From the
Nucleotide Sequences of cDNA Clones Encoding Polypeptides
Homologous to Chorismate Mutases

| | Percent Identity to | |
|---|---|---|
| SEQ ID NO. | 1168940 | 5732016 |
| 12 | 63.9 | 49.1 |
| 14 | 70.0 | 50.6 |
| 16 | 49.0 | 59.8 |
| 18 | 45.4 | 58.0 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire corn and soybean and nearly entire rice and wheat chorismate mutases. These sequences represent the first corn, rice, soybean, and wheat sequences encoding chorismate mutases.

Example 4

Characterization of cDNA Clones Encoding Prephenate Dehydrogenase

The BLASTX search using the EST sequence from the clone listed in Table 6 revealed similarity of the polypeptides encoded by the cDNAs to prephenate dehydrogenase from *Schizosaccharomyces pombe* (NCBI General Identifier No. 3184059). Shown in Table 6 is the BLAST result for the individual EST ("EST"):

TABLE 6

BLAST Results for Sequences Encoding Polypeptides
Homologous to Prephenate Dehydrogenase

| Clone | Status | BLAST pLog Score 3184059 |
|---|---|---|
| sls2c.pk004.f4 | EST | 72.70 |

The sequence of the entire cDNA in clone sls2c.pk004.f4 was determined. The BLASTP search using the nucleotide sequences from the clone listed in Table 7 revealed similarity of the polypeptides encoded by the cDNAs to prephenate dehydrogenase from *Saccharomyces cerevisiae* (NCBI General Identifier No. 6319643). Shown in Table 7 are the BLAST results for the sequences of the entire cDNA insert comprising the indicated cDNA clone ("FIS"):

TABLE 7

BLAST Results for Sequences Encoding Polypeptides
Homologous to Prephenate Dehydrogenase

| Clone | Status | BLAST pLog Score 6319643 |
|---|---|---|
| sls2c.pk004.f4:fis | FIS | 103.00 |

The data in Table 8 represents a calculation of the percent identity of the amino acid sequences set forth in SEQ ID NO:20 and the *Saccharomyces cerevisiae* sequence (NCBI General Identifier No. 6319643).

TABLE 8

Percent Identity of Amino Acid Sequences Deduced From the
Nucleotide Sequences of cDNA Clones Encoding Polypeptides
Homologous to Prephenate Dehydrogenase

| SEQ ID NO. | Percent Identity to 6319643 |
|---|---|
| 20 | 53.3 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a soybean prephenate dehydrogenase. This sequence represents the first plant sequence encoding prephenate dehydrogenase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Tyrosine Biosynthetic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for chorismate mutase are presented by Cotton and Gibson (1968) *Biochim. Biophys. Acta* 156:187–189. Assays for prephenate dehydrogenase are presented by Fischer and Jensen (1987) *Methods Enzymol.* 142:503–507.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having chorismate mutase activity, wherein the amino acid sequence of the polypeptide and the amino acid sequence of SEQ ID NO:12 have at least 80% sequence identity, based on the Clustal alignment method with multiple alignment default parameters of GAP PENALTY=10 and GAP LENGTH PENALTY=10 and pairwise alignment default parameters of KTUPLE=1, GAP PENALTY=3, WINDOW=5 and DIAGONALS SAVED=5, or
   (b) the complement of the nucleotide sequence, wherein the complement and the nucleotide sequence contain the same number of nucleotides and are 100% complementary.

2. The polynucleotide of claim 1 wherein the sequence identity is at least 90%.

3. The polynucleotide of claim 1 wherein the sequence identity is at least 95%.

4. The polynucleotide of claim 1 wherein the polynucleotide encodes the polypeptide of SEQ ID NO:12.

5. The polynucleotide of claim 1 that comprises the nucleotide sequence of SEQ ID NO:11.

6. A recombinant DNA construct comprising the polynucleotide of claim 1 operably linked to at least one regulatory sequence.

7. A cell comprising the polynucleotide of claim 1.

8. The cell of claim 7, wherein the cell is selected from the group consisting of a yeast cell, a bacterial cell and a plant cell.

9. A transgenic plant comprising the polynucleotide of claim 1.

10. A virus comprising the polynucleotide of claim 1.

11. A method for transforming a cell comprising introducing into a cell the polynucleotide of claim 1.

12. A method for producing a transgenic plant comprising (a) transforming a plant cell with the polynucleotide of claim 1 and (b) regenerating a plant from the transformed plant cell.

13. A vector comprising the polynucleotide of claim 1.

14. A seed comprising the recombinant DNA construct of claim 6.

* * * * *

UNITED STATES PATENT AND TRADEMARK OFFICE
CERTIFICATE OF CORRECTION

PATENT NO. : 6,627,798 B2
DATED : September 30, 2003
INVENTOR(S) : Saverio Carl Falco and Omolayo O. Famodu It is certified that error appears in the above-identified patent and that said Letters Patent is hereby corrected as shown below:

<u>Title page,</u>
Item [75], Inventors, delete "Jian-Ming Lee, West Caldwell, NJ (US)"

Signed and Sealed this

Twenty-second Day of June, 2004

JON W. DUDAS
*Acting Director of the United States Patent and Trademark Office*

SEQUENCE LISTING

```
<160> NUMBER OF SEQ ID NOS: 22

<210> SEQ ID NO 1
<211> LENGTH: 552
<212> TYPE: DNA
<213> ORGANISM: Zea mays
<220> FEATURE:
<221> NAME/KEY: unsure
<222> LOCATION: (442)
<220> FEATURE:
<221> NAME/KEY: unsure
<222> LOCATION: (456)
<220> FEATURE:
<221> NAME/KEY: unsure
<222> LOCATION: (460)
<220> FEATURE:
<221> NAME/KEY: unsure
<222> LOCATION: (472)
```

```
<220> FEATURE:
<221> NAME/KEY: unsure
<222> LOCATION: (486)
<220> FEATURE:
<221> NAME/KEY: unsure
<222> LOCATION: (494)..(495)
<220> FEATURE:
<221> NAME/KEY: unsure
<222> LOCATION: (513)
<220> FEATURE:
<221> NAME/KEY: unsure
<222> LOCATION: (518)
<220> FEATURE:
<221> NAME/KEY: unsure
<222> LOCATION: (522)
<220> FEATURE:
<221> NAME/KEY: unsure
<222> LOCATION: (534)

<400> SEQUENCE: 1
cggcattttc cttgcccaac gtgctctccc tcccatttcc tgcgaggtgg ttggtggcga     60
tggccttcaa gctgatcacc aagcccgcgg cggcgtcgcc cgctgctgct tactggggag    120
atctcgcccg ggggccgcag ggtacgagcc gcgttgcctt cggaccagcg cccaggaaca    180 agggctccg cgcggccaac aactccgcaa cgcccatagc taaggtagag agggttgatc     240
gaagtgacat attgacattg gatagcatca gacaagtttt gattagacta gaagacagca    300
tcatatttgg ccttttggag agagcacagt tttgttacaa tgctgataca tatgatagca    360
atgctttcca catggatggt tttggaggat cttggttgaa tatagttaga gaactgagaa    420
gctccatgca caggtgggag ancaagagcc agtganaccn tctttccaag antgctagcc    480
cggtgnacta tcannccagg gttgaccatg cgntcatnat anacaaggtt gaangattgg    540
actctcaaat gg                                                        552

<210> SEQ ID NO 2
<211> LENGTH: 93
<212> TYPE: PRT
<213> ORGANISM: Zea mays

<400> SEQUENCE: 2

Pro Ala Pro Arg Asn Lys Gly Leu Arg Ala Ala Asn Asn Ser Ala Thr
  1               5                  10                  15

Pro Ile Ala Lys Val Glu Arg Val Asp Arg Ser Asp Ile Leu Thr Leu
             20                  25                  30

Asp Ser Ile Arg Gln Val Leu Ile Arg Leu Glu Asp Ser Ile Ile Phe
         35                  40                  45

Gly Leu Leu Glu Arg Ala Gln Phe Cys Tyr Asn Ala Asp Thr Tyr Asp
     50                  55                  60

Ser Asn Ala Phe His Met Asp Gly Phe Gly Gly Ser Trp Leu Asn Ile
 65                  70                  75                  80

Val Arg Glu Leu Thr Glu Lys Leu His Ala Gln Val Gly
                 85                  90

<210> SEQ ID NO 3
<211> LENGTH: 601
<212> TYPE: DNA
<213> ORGANISM: Oryza sativa
<220> FEATURE:
<221> NAME/KEY: unsure
<222> LOCATION: (421)
<220> FEATURE:
<221> NAME/KEY: unsure
<222> LOCATION: (435)
<220> FEATURE:
```

<221> NAME/KEY: unsure
<222> LOCATION: (459)
<220> FEATURE:
<221> NAME/KEY: unsure
<222> LOCATION: (490)
<220> FEATURE:
<221> NAME/KEY: unsure
<222> LOCATION: (507)
<220> FEATURE:
<221> NAME/KEY: unsure
<222> LOCATION: (526)
<220> FEATURE:
<221> NAME/KEY: unsure
<222> LOCATION: (547)
<220> FEATURE:
<221> NAME/KEY: unsure
<222> LOCATION: (566)
<220> FEATURE:
<221> NAME/KEY: unsure
<222> LOCATION: (579)..(580)
<220> FEATURE:
<221> NAME/KEY: unsure
<222> LOCATION: (582)

<400> SEQUENCE: 3

```
tgtatccacc cctccctccc tcccgacgac gtccacccta ccaaccccgg attccattgc      60
gcgcgagcgt gcgagctatg gagttcaaca aggtggtctc cagctacagg gccgcctcgc     120
ccgcgcccgt ggggatggcc cgcggggaag gagggccggc cagccgcgtg gagttcgtcc     180
cgtcgtcgcg gcgggcgcgg ctcgcggcca ccaacaactc cgtcacccc gtgaccaagg      240
aggagaaaca gaggatagat caaagtgaaa tactgacctt ggacaacatt agaacctcct    300
tggttaggca agaagacagc atcatattca gcctcttaga gagagcacag ttttgctaca    360
aatgctgata tatatgataa aaatgctttc catgttggat ggatttgatg gcctttggtt    420
naaattcatg gttangagaa aaccgaaaaa ctacatcanc aagtttggga gatacaagag    480
ccctgatgan caccattctt tccggangat ctgcctgaac aatgtngcaa cctcccccagt   540
atccaanggt ttgcatccaa atggcngatt ccataatann ancaggagat tggaaattat    600
t                                                                     601
```

<210> SEQ ID NO 4
<211> LENGTH: 62
<212> TYPE: PRT
<213> ORGANISM: Oryza sativa
<220> FEATURE:
<221> NAME/KEY: UNSURE
<222> LOCATION: (49)
<220> FEATURE:
<221> NAME/KEY: UNSURE
<222> LOCATION: (58)

<400> SEQUENCE: 4

```
Lys Gln Arg Ile Asp Gln Ser Glu Ile Leu Thr Leu Asp Asn Ile Arg
  1               5                  10                  15

Thr Ser Leu Val Arg Gln Glu Asp Ser Ile Ile Phe Ser Leu Leu Glu
             20                  25                  30

Arg Ala Gln Phe Ala Thr Asn Ala Asp Ile Tyr Asp Lys Asn Ala Phe
         35                  40                  45

Xaa Leu Asp Gly Phe Asp Gly Leu Trp Xaa Lys Phe Met Val
     50                  55                  60
```

<210> SEQ ID NO 5
<211> LENGTH: 525
<212> TYPE: DNA
<213> ORGANISM: Glycine max

```
<220> FEATURE:
<221> NAME/KEY: unsure
<222> LOCATION: (432)
<220> FEATURE:
<221> NAME/KEY: unsure
<222> LOCATION: (514)
<220> FEATURE:
<221> NAME/KEY: unsure
<222> LOCATION: (516)

<400> SEQUENCE: 5
agcttaattt caagaatggc caaagcagca gaacaaagtc ctgattctgg gaatgtgtac      60
acgctagctt ctgtgagaga ggatttggtt aggcaagagg ataccatcat ttatggtctc     120
attgagagag ccaagttccc tagcaattct cacacctatg atgaaaagta tgctcaaatc     180
cagggttttt gtggctcatt ggtggaattt gttgttaaga atacagaggc cattcaagct     240
aaggctggaa gatacaaaaa ccctgaagaa acgccttct tcccagaaaa tttaccacca     300
tcaattgtgc catcttactc cttcaaacag ttttttgcatc ctggtgctgc ttcaattaac    360
ataaacaagt catctgggaa aatgtatttc aaagagttac ttccattgct tgctacttcg     420
ggtgatgatg gnaactatgc gcaaaactgc agctaatgac cttcattatt gcagtcatct    480
ctagaaggat cactatggaa agtttgtagc tgangngaaa tcagg                    525

<210> SEQ ID NO 6
<211> LENGTH: 132
<212> TYPE: PRT
<213> ORGANISM: Glycine max

<400> SEQUENCE: 6

Asp Ser Gly Asn Val Tyr Thr Leu Ala Ser Val Arg Glu Asp Leu Val
  1               5                  10                  15

Arg Gln Glu Asp Thr Ile Ile Tyr Gly Leu Ile Glu Arg Ala Lys Phe
             20                  25                  30

Pro Ser Asn Ser His Thr Tyr Asp Glu Lys Tyr Ala Gln Ile Gln Gly
         35                  40                  45

Phe Cys Gly Ser Leu Val Glu Phe Val Val Lys Asn Thr Glu Ala Ile
 50                  55                  60

Gln Ala Lys Ala Gly Arg Tyr Lys Asn Pro Glu Glu Asn Ala Phe Phe
 65                  70                  75                  80

Pro Glu Asn Leu Pro Pro Ser Ile Val Pro Ser Tyr Ser Phe Lys Gln
                 85                  90                  95

Phe Leu His Pro Gly Ala Ala Ser Ile Asn Ile Asn Lys Ser Ser Gly
            100                 105                 110

Lys Met Tyr Phe Lys Glu Leu Leu Pro Leu Leu Ala Thr Ser Gly Asp
        115                 120                 125

Asp Gly Asn Tyr
    130

<210> SEQ ID NO 7
<211> LENGTH: 579
<212> TYPE: DNA
<213> ORGANISM: Triticum aestivum
<220> FEATURE:
<221> NAME/KEY: unsure
<222> LOCATION: (417)
<220> FEATURE:
<221> NAME/KEY: unsure
<222> LOCATION: (484)
<220> FEATURE:
<221> NAME/KEY: unsure
<222> LOCATION: (536)
```

```
<220> FEATURE:
<221> NAME/KEY: unsure
<222> LOCATION: (551)
<220> FEATURE:
<221> NAME/KEY: unsure
<222> LOCATION: (565)
<220> FEATURE:
<221> NAME/KEY: unsure
<222> LOCATION: (577)

<400> SEQUENCE: 7
ccgagttctt cgttcgggaa gccgaggtcc tgcacgccaa ggctggacac tatcaaaagc      60
cagaagatgt tccattcttc tctcaagatc ttccaccacc tgtctttcct accaaaggtc    120
gcccaaaggt tttgcaccct tttgcttcat tggtctgtgt gaatgatgca atatggaaga    180
tgtatttcaa tgaattgcta ccattattca ctgcggatgg cgatgatggc aactatgcag    240
aaacagttgc attagatttt gcatgtctgc aggctctctc aagaagaatt cattgtggca    300
aatatgttgc tgaggtgaaa ttcaaagacg cgcctcaaga ttatagccca ccaatacgtg    360
ctaaggacac taatgctctg atgaacttac taacgttcac ggctgttgaa gaaaaggtca    420
agaagagagt agagaagaag gcaaggatat ttggacagaa tgtcactctg gaggacagtg    480
taggcaagca agatggtgat gcctgtgaca gtcactgtaa agttgattcc aaagtgcttt    540
ctaagctata tgatatgtgg ggaatgccct ttaacgaag                            579

<210> SEQ ID NO 8
<211> LENGTH: 154
<212> TYPE: PRT
<213> ORGANISM: Triticum aestivum

<400> SEQUENCE: 8

Glu Phe Phe Val Arg Glu Ala Glu Val Leu His Ala Lys Ala Gly His
  1               5                  10                  15

Tyr Gln Lys Pro Glu Asp Val Pro Phe Phe Ser Gln Asp Leu Pro Pro
                 20                  25                  30

Pro Val Phe Pro Thr Lys Gly Arg Pro Lys Val Leu His Pro Phe Ala
             35                  40                  45

Ser Leu Val Cys Val Asn Asp Ala Ile Trp Lys Met Tyr Phe Asn Glu
         50                  55                  60

Leu Leu Pro Leu Phe Thr Ala Asp Gly Asp Gly Asn Tyr Ala Glu
 65                  70                  75                  80

Thr Val Ala Leu Asp Phe Ala Cys Leu Gln Ala Leu Ser Arg Arg Ile
                 85                  90                  95

His Cys Gly Lys Tyr Val Ala Glu Val Lys Phe Lys Asp Ala Pro Gln
            100                 105                 110

Asp Tyr Ser Pro Pro Ile Arg Ala Lys Asp Thr Asn Ala Leu Met Asn
        115                 120                 125

Leu Leu Thr Phe Thr Ala Val Glu Glu Lys Val Lys Lys Arg Val Glu
    130                 135                 140

Lys Lys Ala Arg Ile Phe Gly Gln Asn Val
145                 150

<210> SEQ ID NO 9
<211> LENGTH: 550
<212> TYPE: DNA
<213> ORGANISM: Glycine max
<220> FEATURE:
<221> NAME/KEY: unsure
<222> LOCATION: (328)
```

```
<400> SEQUENCE: 9
ctcatgcaaa gctcctgaga tagcagcatt tgagaaatat ctacctcctg atgttgaaat      60
cgtatcttgc cattccctcc acggtcccaa tgttgatcct cgaggtcaac ctcttgtctt     120
gatcaaacat cgtgcttctc aagaaagttt cgaaaaagtc gagcatgtac tctcctgcct     180
cggctccaaa cagcatgtcc tctcagcatc tcagcacgac cgtatcacag cagataccca     240
agccgtcacc catgcagcct tcctatccat gggtaaagcc tggcacgcca accttcaatt     300
tccctgggag atagcccgtt acgttggngg tatcgaaaac gtcaaaatca atctgactct     360
tcgtatttat tctcaaaaat ggcatgtcta cgccggtctc gccatcctga acccttatgc     420
caaagaacag attagagagt atgcacaaag cgtgacaaga tctatataag ttgatgctgg     480
gagggcaccg aagagagcta aagaagcga atcaagagtg caggacgatt tgtctttgct     540
gggcgcaaaa                                                            550

<210> SEQ ID NO 10
<211> LENGTH: 152
<212> TYPE: PRT
<213> ORGANISM: Glycine max

<400> SEQUENCE: 10

Ser Cys Lys Ala Pro Glu Ile Ala Ala Phe Glu Lys Tyr Leu Pro Pro
  1               5                  10                  15

Asp Val Glu Ile Val Ser Cys His Ser Leu His Gly Pro Asn Val Asp
                 20                  25                  30

Pro Arg Gly Gln Pro Leu Val Leu Ile Lys His Arg Ala Ser Gln Glu
             35                  40                  45

Ser Phe Glu Lys Val Glu His Val Leu Ser Cys Leu Gly Ser Lys Gln
         50                  55                  60

His Val Leu Ser Ala Ser Gln His Asp Arg Ile Thr Ala Asp Thr Gln
 65                  70                  75                  80

Ala Val Thr His Ala Ala Phe Leu Ser Met Gly Lys Ala Trp His Ala
                 85                  90                  95

Asn Leu Gln Phe Pro Trp Glu Ile Ala Arg Tyr Val Gly Gly Ile Glu
            100                 105                 110

Asn Val Lys Ile Asn Leu Thr Leu Arg Ile Tyr Ser Gln Lys Trp His
        115                 120                 125

Val Tyr Ala Gly Leu Ala Ile Leu Asn Pro Tyr Ala Lys Glu Gln Ile
    130                 135                 140

Arg Glu Tyr Ala Gln Ser Val Thr
145                 150

<210> SEQ ID NO 11
<211> LENGTH: 1223
<212> TYPE: DNA
<213> ORGANISM: Zea mays

<400> SEQUENCE: 11
cggcattttc cttgcccaac gtgctctccc tcccatttcc tgcgaggtgg ttggtggcga      60
tggccttcaa gctgatcacc aagcccgcgc ggcgtcgcc cgctgctgct tactggggag     120
atctcgcccg ggggccgcag ggtacgagcc gcgttgcctt cggaccagcg cccaggaaca     180
aggggctccg cgcggccaac aactccgcaa cgcccatagc taaggtagag agggttgatc     240
gaagtgacat attgacattg gatagcatca gacaagtttt gattagacta aagacagca     300
tcatatttgg cctttggag agagcacagt tttgttacaa tgctgataca tatgatagca     360
```

```
atgctttcca catggatggt tttggaggat ctttggttga atatatagtt agagaaactg    420
aaaagctcca tgcacaggtt gggagataca agagcccaga tgagcaccct ttcttttcca    480
aggatctgcc tgagccccgg ttgccaccta tgcaataccc aagggttttg catcccattg    540
ctgattctat caatatcaac aaagagattt ggaaaatgta ttttgatgaa cttcttccaa    600
gattggtgaa agaaggaagt gatggtaatg ctggatccag tgctctttgt gacacaacct    660
gcttgcaggc actctccaga aggatccact atgggaagtt tgtggcagag gccaagtttc    720
aagagtcccc tgaagcttac acgccagcca ataatagccca agaccgtgat caactcatga    780
accttctcac atatgaaacg gtggagcgtg ctatcgaaca agggtggag gccaaagcca    840 agatcttcgg gcaagaggtg aacattggtg ctaaggacaa cggcagccca ccggtctaca    900
aaatcaggcc gagcttggtc gccgagctgt acagctacag aatcatgccg ctaaccaagg    960
aggttgaggt cgcgtacttg cttaagaggc tggattgagt gtgtttacgt agctgtaaaa   1020
ctgccagatc cgaactcctg gtattaaacc ataacatcgg taagtaccca tttctgtgaa   1080
gaggatgatc cgaactcctg tcattaaacc agaaacatcag taagtaccca gttttgggga   1140
gaggatggaa aatataccat gtgtggcaag caacatgcat aatatcatct ggagttgcgc   1200
ttaaaaaaaa aaaaaaaaaa aac                                           1223
```

<210> SEQ ID NO 12
<211> LENGTH: 331
<212> TYPE: PRT
<213> ORGANISM: Zea mays

<400> SEQUENCE: 12

```
Ala Phe Ser Leu Pro Asn Val Leu Ser Leu Pro Phe Pro Ala Arg Trp
  1               5                  10                  15

Leu Val Ala Met Ala Phe Lys Leu Ile Thr Lys Pro Ala Ala Ala Ser
             20                  25                  30

Pro Ala Ala Ala Tyr Trp Gly Asp Leu Ala Arg Gly Pro Gln Gly Thr
         35                  40                  45

Ser Arg Val Ala Phe Gly Pro Ala Pro Arg Asn Lys Gly Leu Arg Ala
     50                  55                  60

Ala Asn Asn Ser Ala Thr Pro Ile Ala Lys Val Glu Arg Val Asp Arg
 65                  70                  75                  80

Ser Asp Ile Leu Thr Leu Asp Ser Ile Arg Gln Val Leu Ile Arg Leu
                 85                  90                  95

Glu Asp Ser Ile Ile Phe Gly Leu Leu Glu Arg Ala Gln Phe Cys Tyr
            100                 105                 110

Asn Ala Asp Thr Tyr Asp Ser Asn Ala Phe His Met Asp Gly Phe Gly
        115                 120                 125

Gly Ser Leu Val Glu Tyr Ile Val Arg Glu Thr Glu Lys Leu His Ala
    130                 135                 140

Gln Val Gly Arg Tyr Lys Ser Pro Asp Glu His Pro Phe Phe Ser Lys
145                 150                 155                 160

Asp Leu Pro Glu Pro Arg Leu Pro Met Gln Tyr Pro Arg Val Leu
                165                 170                 175

His Pro Ile Ala Asp Ser Ile Asn Ile Asn Lys Glu Ile Trp Lys Met
            180                 185                 190

Tyr Phe Asp Glu Leu Leu Pro Arg Leu Val Lys Glu Gly Ser Asp Gly
        195                 200                 205

Asn Ala Gly Ser Ser Ala Leu Cys Asp Thr Thr Cys Leu Gln Ala Leu
```

```
    210                 215                 220
Ser Arg Arg Ile His Tyr Gly Lys Phe Val Ala Glu Ala Lys Phe Gln
225                 230                 235                 240

Glu Ser Pro Glu Ala Tyr Thr Pro Ala Ile Ile Ala Gln Asp Arg Asp
                245                 250                 255

Gln Leu Met Asn Leu Leu Thr Tyr Glu Thr Val Glu Arg Ala Ile Glu
            260                 265                 270

His Arg Val Glu Ala Lys Ala Lys Ile Phe Gly Gln Glu Val Asn Ile
        275                 280                 285

Gly Ala Lys Asp Asn Gly Ser Pro Pro Val Tyr Lys Ile Arg Pro Ser
    290                 295                 300

Leu Val Ala Glu Leu Tyr Ser Tyr Arg Ile Met Pro Leu Thr Lys Glu
305                 310                 315                 320

Val Glu Val Ala Tyr Leu Leu Lys Arg Leu Asp
                325                 330

<210> SEQ ID NO 13
<211> LENGTH: 1231
<212> TYPE: DNA
<213> ORGANISM: Oryza sativa

<400> SEQUENCE: 13
gcacgagtgt atccacccct ccctccctcc cgacgacgtc caccctacca accccggatt      60
ccattgcgcg cgagcgtgcg agctatggag ttcaacaagg tggtctccag ctacagggcc     120
gcctcgcccg cgcccgtggg gatggcccgc gggggaggag ggccggccag ccgcgtggag     180
ttcgtcccgt cgtcgcggcg ggcgcggctc gcggccacca caactccgt caccccgtg      240 accaaggagg agaaacagag gatagatcaa agtgaaatac tgaccttgga caacattaga     300
acctccttgg ttaggcaaga agacagcatc atattcagcc tcttagagag agcacagttt     360
tgctacaatg ctgatatata tgataaaaat gctttccatg tggatggatt tgatggctct     420
ttggttgaat tcatggttag agaaaccgaa aaactacatc aacaggttgg agatacaaag     480
agccctgatg agcacccatt ctttccggag gatctgcctg aaccactgtt gccacctctc     540
cagtatccaa aggttttgca tcctattgct gattctatta atatcaacaa ggagatttgg     600
aaaatgtatt ttgatgagct tcttccaaga ttagtgaaag aaggaagtga tggtaattat     660
ggatccagtg ctctttgtga cacgatctgc ttgcaggcgc tctccaaaag aattcactat     720
ggtaagtttg tggcagaggc taagtttcaa gagtctcctg aagcttacat gcctgcgata     780
atagcacagg actgcgatca actaatgcac ctcctcacct atgaaacggt ggagcgtgct     840
attgaacata gggtggaagc taaggctaag atctttggac aggaggtgga tttaggcgct     900
gaagacaacg gcgctccacc aatgtacaag ataaggccca gtttggtggc tgaactgtac     960
agctacagga tcatgccgct aaccaaggag gttcaagtag cctacttgct gaggagattg    1020
gattgattgt ttacgattgt aaactgccag cttcggtttc ctggcatcaa agaataaatt    1080 agggaaaga caaccatagg tatccatttt gggacaactg aaagaaaata ttttattcgg    1140
gtttacacta tattttgtgg caagaacaag cagaagcagg atatcacatg aaatgatatg    1200
gagatgttgc atataaaaaa aaaaaaaaaa a                                   1231

<210> SEQ ID NO 14
<211> LENGTH: 257
<212> TYPE: PRT
<213> ORGANISM: Oryza sativa
```

<400> SEQUENCE: 14

```
Lys Gln Arg Ile Asp Gln Ser Glu Ile Leu Thr Leu Asp Asn Ile Arg
 1               5                  10                  15
Thr Ser Leu Val Arg Gln Glu Asp Ser Ile Ile Phe Ser Leu Leu Glu
            20                  25                  30
Arg Ala Gln Phe Cys Tyr Asn Ala Asp Ile Tyr Asp Lys Asn Ala Phe
        35                  40                  45
His Val Asp Gly Phe Asp Gly Ser Leu Val Glu Phe Met Val Arg Glu
    50                  55                  60
Thr Glu Lys Leu His Gln Gln Val Gly Arg Tyr Lys Ser Pro Asp Glu
 65                  70                  75                  80
His Pro Phe Phe Pro Glu Asp Leu Pro Glu Pro Leu Leu Pro Pro Leu
                85                  90                  95
Gln Tyr Pro Lys Val Leu His Pro Ile Ala Asp Ser Ile Asn Ile Asn
            100                 105                 110
Lys Glu Ile Trp Lys Met Tyr Phe Asp Glu Leu Leu Pro Arg Leu Val
        115                 120                 125
Lys Glu Gly Ser Asp Gly Asn Tyr Gly Ser Ser Ala Leu Cys Asp Thr
    130                 135                 140
Ile Cys Leu Gln Ala Leu Ser Lys Arg Ile His Tyr Gly Lys Phe Val
145                 150                 155                 160
Ala Glu Ala Lys Phe Gln Glu Ser Pro Glu Ala Tyr Met Pro Ala Ile
                165                 170                 175
Ile Ala Gln Asp Cys Asp Gln Leu Met His Leu Leu Thr Tyr Glu Thr
            180                 185                 190
Val Glu Arg Ala Ile Glu His Arg Val Glu Ala Lys Ala Lys Ile Phe
        195                 200                 205
Gly Gln Glu Val Asp Leu Gly Ala Glu Asp Asn Gly Ala Pro Pro Met
    210                 215                 220
Tyr Lys Ile Arg Pro Ser Leu Val Ala Glu Leu Tyr Ser Tyr Arg Ile
225                 230                 235                 240
Met Pro Leu Thr Lys Glu Val Gln Val Ala Tyr Leu Leu Arg Arg Leu
                245                 250                 255
Asp
```

<210> SEQ ID NO 15
<211> LENGTH: 1020
<212> TYPE: DNA
<213> ORGANISM: Glycine max

<400> SEQUENCE: 15

```
gcacgagagc ttaatttcaa gaatggccaa agcagcagaa caaagtcctg attctgggaa    60
tgtgtacacg ctagcttctg tgagagagga tttggttagg caagaggata ccatcattta   120
tggtctcatt gagagagcca agttccctag caattctcac acctatgatg aaaagtatgc   180
tcaaatccag ggttttttgtg gctcattggt ggaatttgtt gttaagaata cagaggccat   240
tcaagctaag gctggaagat acaaaaaccc tgaagaaaac gccttcttcc cagaaaattt   300
accaccatca attgtgccat cttactcctt caaacagttt ttgcatcctg gtgctgcttc   360
aattaacata aacaagtcca tctggaaaat gtatttcaaa gagttacttc cattgcttgc   420
tacttcgggt gatgatggca actatgcgca aactgcagct aatgaccttt cattattgca   480
gtccatctct agaaggattc actatggaaa gtttgtagct gaggtgaaat tcagggatgc   540
tcctcaagac tacgagcctt taattcgagc taaggataaa gaaggattga tgaaattgtt   600
```

-continued

```
gacatttaca agcgttgaag agacggtgag gaagagagtt gaaagaagg ctgtggtgtt      660 tgggcaggaa gtgaatctta acagtgatga caatgacaat gaaaccgta aatttgatcc      720 atcagtggct tctagcttgt acaaaaattg ggtgatacct ctcaccaagg aggttcaggt      780
tgagtacctc ttgcgccgtc tagactgaag gcattacaat gcagttagaa tttagaagaa      840
tggaagatga atatgatgtt gttgttcaaa tgattaagct cttaagtgat cctttattgc      900
caacttcatg tagctgttga ttcagaaata ttatttgtag ctatagattg ttacctttat      960
tttcatcggc tttattagga aaaggcatta ttatatcatg atcttcaaaa aaaaaaaaaa     1020
```

<210> SEQ ID NO 16
<211> LENGTH: 261
<212> TYPE: PRT
<213> ORGANISM: Glycine max

<400> SEQUENCE: 16

```
Met Ala Lys Ala Ala Glu Gln Ser Pro Asp Ser Gly Asn Val Tyr Thr
  1               5                  10                  15

Leu Ala Ser Val Arg Glu Asp Leu Val Arg Gln Glu Asp Thr Ile Ile
             20                  25                  30

Tyr Gly Leu Ile Glu Arg Ala Lys Phe Pro Ser Asn Ser His Thr Tyr
         35                  40                  45

Asp Glu Lys Tyr Ala Gln Ile Gln Gly Phe Cys Gly Ser Leu Val Glu
     50                  55                  60

Phe Val Val Lys Asn Thr Glu Ala Ile Gln Ala Lys Ala Gly Arg Tyr
 65                  70                  75                  80

Lys Asn Pro Glu Glu Asn Ala Phe Phe Pro Glu Asn Leu Pro Pro Ser
                 85                  90                  95

Ile Val Pro Ser Tyr Ser Phe Lys Gln Phe Leu His Pro Gly Ala Ala
            100                 105                 110

Ser Ile Asn Ile Asn Lys Ser Ile Trp Lys Met Tyr Phe Lys Glu Leu
        115                 120                 125

Leu Pro Leu Leu Ala Thr Ser Gly Asp Asp Gly Asn Tyr Ala Gln Thr
    130                 135                 140

Ala Ala Asn Asp Leu Ser Leu Leu Gln Ser Ile Ser Arg Arg Ile His
145                 150                 155                 160

Tyr Gly Lys Phe Val Ala Glu Val Lys Phe Arg Asp Ala Pro Gln Asp
                165                 170                 175

Tyr Glu Pro Leu Ile Arg Ala Lys Asp Lys Glu Gly Leu Met Lys Leu
            180                 185                 190

Leu Thr Phe Thr Ser Val Glu Glu Thr Val Arg Lys Arg Val Glu Lys
        195                 200                 205

Lys Ala Val Val Phe Gly Gln Glu Val Asn Leu Asn Ser Asp Asp Asn
    210                 215                 220

Asp Asn Glu Asn Arg Lys Phe Asp Pro Ser Val Ala Ser Ser Leu Tyr
225                 230                 235                 240

Lys Asn Trp Val Ile Pro Leu Thr Lys Glu Val Gln Val Glu Tyr Leu
                245                 250                 255

Leu Arg Arg Leu Asp
            260
```

<210> SEQ ID NO 17
<211> LENGTH: 780
<212> TYPE: DNA
<213> ORGANISM: Triticum aestivum

<400> SEQUENCE: 17

```
gcacgagccg agttcttcgt tcgggaagcc gaggtcctgc acgccaaggc tggacactat    60
caaaagccag aagatgttcc attcttctct caagatcttc caccacctgt ctttcctacc   120
aaaggtcgcc caaggttttt gcacccttttt gcttcattgg tctgtgtgaa tgatgcaata   180
tggaagatgt atttcaatga attgctacca ttattcactg cggatggcga tgatggcaac   240
tatgcagaaa cagttgcatt agattttgca tgtctgcagg ctctctcaag aagaattcat   300
tgtggcaaat atgttgctga ggtgaaattc aaagacgcgc tcaagatta tagcccacca   360
atacgtgcta aggacactaa tgctctgatg aacttactaa cgttcacggc tgttgaagaa   420
aaggtcaaga agagagtaga gaagaaggca aggatatttg gacagaatgt cactctggag   480
gacagtgtag gcaagcaaga tggtgatgcc tgtgacagtc actgtaaagt tgatccaaaa   540
gtgctttcta agctatatga tatgtgggta atgcctttaa cgaaggatgt tgaagtcgaa   600
tatcttctcc ggcgtcttga ctgattcgcc caataatttc aaatataaat atgttgcatg   660
cttttgagct tgctatatgt atgaaacaaa ttcaagaggc tttcttgaat gtgagacatc   720
acgaaatcca taaatttgt tcaaaaaaaa aaaaaaaaa aaaaaaaaaa aaaaaaaa       780
```

<210> SEQ ID NO 18
<211> LENGTH: 207
<212> TYPE: PRT
<213> ORGANISM: Triticum aestivum

<400> SEQUENCE: 18

```
Ala Arg Ala Glu Phe Phe Val Arg Glu Ala Glu Val Leu His Ala Lys
  1               5                  10                  15

Ala Gly His Tyr Gln Lys Pro Glu Asp Val Pro Phe Phe Ser Gln Asp
                 20                  25                  30

Leu Pro Pro Val Phe Pro Thr Lys Gly Arg Pro Lys Val Leu His
             35                  40                  45

Pro Phe Ala Ser Leu Val Cys Val Asn Asp Ala Ile Trp Lys Met Tyr
         50                  55                  60

Phe Asn Glu Leu Leu Pro Leu Phe Thr Ala Asp Gly Asp Asp Gly Asn
 65                  70                  75                  80

Tyr Ala Glu Thr Val Ala Leu Asp Phe Ala Cys Leu Gln Ala Leu Ser
                 85                  90                  95

Arg Arg Ile His Cys Gly Lys Tyr Val Ala Glu Val Lys Phe Lys Asp
                100                 105                 110

Ala Pro Gln Asp Tyr Ser Pro Pro Ile Arg Ala Lys Asp Thr Asn Ala
            115                 120                 125

Leu Met Asn Leu Leu Thr Phe Thr Ala Val Glu Glu Lys Val Lys Lys
        130                 135                 140

Arg Val Glu Lys Lys Ala Arg Ile Phe Gly Gln Asn Val Thr Leu Glu
145                 150                 155                 160

Asp Ser Val Gly Lys Gln Asp Gly Asp Ala Cys Asp Ser His Cys Lys
                165                 170                 175

Val Asp Pro Lys Val Leu Ser Lys Leu Tyr Asp Met Trp Val Met Pro
            180                 185                 190

Leu Thr Lys Asp Val Glu Val Glu Tyr Leu Leu Arg Arg Leu Asp
        195                 200                 205
```

<210> SEQ ID NO 19
<211> LENGTH: 1198

<212> TYPE: DNA
<213> ORGANISM: Glycine max

<400> SEQUENCE: 19

| | | | | | |
|---|---|---|---|---|---|
| gcacgagctc | atgcaaagct | cctgagatag | cagcatttga | aaatatcta | cctcctgatg | 60 |
| ttgaaatcgt | atcttgccat | tccctccacg | gtcccaatgt | tgatcctcga | ggtcaacctc | 120 |
| ttgtcttgat | caaacatcgt | gcttctcaag | aaagtttcga | aaaagtcgag | catgtactct | 180 |
| cctgcctcgg | ctccaaacag | catgtcctct | cagcatctca | gcacgaccgt | atcacagcag | 240 |
| atacccaagc | cgtcacccat | gcagccttcc | tatccatggg | taaagcctgg | cacgccaacc | 300 |
| ttcaatttcc | ctgggagata | gcccgttacg | ttggaggtat | cgaaaacgtc | aaaatcaatc | 360 |
| tgactcttcg | tatttattct | caaaaatggc | atgtctacgc | cggtctcgcc | atcctgaacc | 420 |
| cttatgccaa | agaacagatt | agagagtatg | cacaaagcgt | gacagatcta | tataagttga | 480 |
| tgctgggagg | gcaccgaaga | gagctagaag | agcgaatcaa | gagtgcagga | cgatttgtct | 540 |
| tgctgggcg | caaaaagtcc | gatgaattac | tcttgcgaga | tgaagtgctt | gatcgttttt | 600 |
| ccttgggcaa | gaaacccgag | aaacctactc | caaataatca | cctctctcta | cttgccattg | 660 |
| tggactgttg | ggcccgtctt | aatattattc | cctacgatca | tatgatctgt | agcacgcctc | 720 |
| tctttcgtct | ttggctcggt | gtctcggaat | atctgtttcg | aaatgagaaa | ttgttagatg | 780 |
| aggttatcaa | tacagctatt | gaagacaaca | cattccgttc | tgatgattta | gagtttacgt | 840 |
| tgcggctag | aggatggagc | gagtgtgtag | agtttggaga | ttttgagagt | tggaaggata | 900 |
| ggtttgaaaa | aacgcaaatg | ttcttcgctc | caagattccc | ggaggcaacg | agagtaggta | 960 |
| atgagatgat | gaagacaatt | ttggcaaata | tcaaggatta | gagttgggga | ctggatagat | 1020 |
| tggggttggg | ttggaggtgg | tttgacttat | ttatctggag | tttggctggc | tgctcgacat | 1080 |
| tcgacatgat | tcgaatttcc | agtagggcgt | aacagagggt | atactgcgct | gtaatttaag | 1140 |
| atgacactct | ttttaaactc | aaggaaaact | ccatttcacg | aaaaaaaaaa | aaaaaaaa | 1198 |

<210> SEQ ID NO 20
<211> LENGTH: 332
<212> TYPE: PRT
<213> ORGANISM: Glycine max

<400> SEQUENCE: 20

Thr Ser Ser Cys Lys Ala Pro Glu Ile Ala Ala Phe Glu Lys Tyr Leu
 1               5                  10                  15

Pro Pro Asp Val Glu Ile Val Ser Cys His Ser Leu His Gly Pro Asn
            20                  25                  30

Val Asp Pro Arg Gly Gln Pro Leu Val Leu Ile Lys His Arg Ala Ser
        35                  40                  45

Gln Glu Ser Phe Glu Lys Val Glu His Val Leu Ser Cys Leu Gly Ser
    50                  55                  60

Lys Gln His Val Leu Ser Ala Ser Gln His Asp Arg Ile Thr Ala Asp
65                  70                  75                  80

Thr Gln Ala Val Thr His Ala Ala Phe Leu Ser Met Gly Lys Ala Trp
                85                  90                  95

His Ala Asn Leu Gln Phe Pro Trp Glu Ile Ala Arg Tyr Val Gly Gly
            100                 105                 110

Ile Glu Asn Val Lys Ile Asn Leu Thr Leu Arg Ile Tyr Ser Gln Lys
        115                 120                 125

Trp His Val Tyr Ala Gly Leu Ala Ile Leu Asn Pro Tyr Ala Lys Glu
    130                 135                 140

```
Gln Ile Arg Glu Tyr Ala Gln Ser Val Thr Asp Leu Tyr Lys Leu Met
145                 150                 155                 160

Leu Gly Gly His Arg Arg Glu Leu Glu Arg Ile Lys Ser Ala Gly
            165                 170                 175

Arg Phe Val Phe Ala Gly Arg Lys Lys Ser Asp Glu Leu Leu Leu Arg
            180                 185                 190

Asp Glu Val Leu Asp Arg Phe Ser Leu Gly Lys Lys Pro Glu Lys Pro
            195                 200                 205

Thr Pro Asn Asn His Leu Ser Leu Leu Ala Ile Val Asp Cys Trp Ala
            210                 215                 220

Arg Leu Asn Ile Ile Pro Tyr Asp His Met Ile Cys Ser Thr Pro Leu
225                 230                 235                 240

Phe Arg Leu Trp Leu Gly Val Ser Glu Tyr Leu Phe Arg Asn Glu Lys
                245                 250                 255

Leu Leu Asp Glu Val Ile Asn Thr Ala Ile Glu Asp Asn Thr Phe Arg
                260                 265                 270

Ser Asp Asp Leu Glu Phe Thr Phe Ala Ala Arg Gly Trp Ser Glu Cys
            275                 280                 285

Val Glu Phe Gly Asp Phe Glu Ser Trp Lys Asp Arg Phe Glu Lys Thr
            290                 295                 300

Gln Met Phe Phe Ala Pro Arg Phe Pro Glu Ala Thr Arg Val Gly Asn
305                 310                 315                 320

Glu Met Met Lys Thr Ile Leu Ala Asn Ile Lys Asp
                325                 330

<210> SEQ ID NO 21
<211> LENGTH: 334
<212> TYPE: PRT
<213> ORGANISM: Arabidopsis thaliana

<400> SEQUENCE: 21

Met Arg Ser Ser Cys Cys Ser Ser Ala Ile Gly Gly Phe Phe Asp His
1               5                   10                  15

Arg Arg Glu Leu Ser Thr Ser Thr Pro Ile Ser Thr Leu Leu Pro Leu
                20                  25                  30

Pro Ser Thr Lys Ser Ser Phe Ser Val Arg Cys Ser Leu Pro Gln Pro
            35                  40                  45

Ser Lys Pro Arg Ser Gly Thr Ser Ser Val His Ala Val Met Thr Leu
    50                  55                  60

Ala Gly Ser Leu Thr Gly Lys Lys Arg Val Asp Glu Ser Glu Ser Leu
65                  70                  75                  80

Thr Leu Glu Gly Ile Arg Asn Ser Leu Ile Arg Gln Glu Asp Ser Ile
                85                  90                  95

Ile Phe Gly Leu Leu Glu Arg Ala Lys Tyr Cys Tyr Asn Ala Asp Thr
            100                 105                 110

Tyr Asp Pro Thr Ala Phe Asp Met Asp Gly Phe Asn Gly Ser Leu Val
            115                 120                 125

Glu Tyr Met Val Lys Gly Thr Glu Lys Leu His Ala Lys Val Gly Arg
130                 135                 140

Phe Lys Ser Pro Asp Glu His Pro Phe Phe Pro Asp Asp Leu Pro Glu
145                 150                 155                 160

Pro Met Leu Pro Pro Leu Gln Tyr Pro Lys Val Leu His Phe Ala Ala
                165                 170                 175

Asp Ser Ile Asn Ile Asn Lys Lys Ile Trp Asn Met Tyr Phe Arg Asp
```

```
                180                 185                 190
Leu Val Pro Arg Leu Val Lys Lys Gly Asp Asp Gly Asn Tyr Gly Ser
            195                 200                 205

Thr Ala Val Cys Asp Ala Ile Cys Leu Gln Cys Leu Ser Lys Arg Ile
210                 215                 220

His Tyr Gly Lys Phe Val Ala Glu Ala Lys Phe Gln Ala Ser Pro Glu
225                 230                 235                 240

Ala Tyr Glu Ser Ala Ile Lys Ala Gln Asp Lys Asp Arg Leu Met Asp
            245                 250                 255

Met Leu Thr Phe Pro Thr Val Glu Asp Ala Ile Lys Lys Arg Val Glu
            260                 265                 270

Met Lys Thr Arg Thr Tyr Gly Gln Glu Val Lys Val Gly Met Glu Glu
            275                 280                 285

Lys Glu Glu Glu Glu Glu Gly Asn Glu Ser His Val Tyr Lys Ile
            290                 295                 300

Ser Pro Ile Leu Val Gly Asp Leu Tyr Gly Asp Trp Ile Met Pro Leu
305                 310                 315                 320

Thr Lys Glu Val Gln Val Glu Tyr Leu Leu Arg Arg Leu Asp
            325                 330

<210> SEQ ID NO 22
<211> LENGTH: 265
<212> TYPE: PRT
<213> ORGANISM: Arabidopsis thaliana

<400> SEQUENCE: 22

Met Ala Arg Val Phe Glu Ser Asp Ser Gly Ser Gly Cys Ser Asn Val
1               5                   10                  15

Leu Ser Leu Asp Leu Ile Arg Glu Ser Leu Ile Arg Gln Glu Asp Thr
            20                  25                  30

Ile Val Phe Ser Leu Ile Glu Arg Ala Lys Phe Pro Leu Asn Ser Pro
            35                  40                  45

Ala Phe Glu Glu Ser Arg Cys Leu Asp Ser Gly Ser Phe Ser Ser Leu
        50                  55                  60

Thr Glu Phe Phe Val Arg Glu Thr Glu Ile Ile Gln Ala Lys Val Gly
65                  70                  75                  80

Arg Tyr Glu Tyr Pro Glu Glu Asn Pro Phe Phe Leu Glu Asn Ile Pro
                85                  90                  95

His Ser Val Phe Pro Thr His Lys Tyr Pro Ser Ala Leu His Pro Lys
            100                 105                 110

Ala Leu Ser Val Asn Ile Asn Lys Gln Ile Trp Asp Ile Tyr Phe Lys
        115                 120                 125

Glu Leu Leu Pro Leu Phe Val Lys Pro Gly Asp Asp Gly Asn Tyr Pro
130                 135                 140

Ser Thr Ala Ala Ser Asp Leu Ala Cys Leu Gln Ala Leu Ser Arg Arg
145                 150                 155                 160

Ile His Tyr Gly Lys Phe Val Ala Glu Val Lys Phe Arg Asp Ala Pro
                165                 170                 175

Gln Asp Tyr Glu Pro Ala Ile Arg Ala Gln Asp Arg Glu Ala Leu Met
            180                 185                 190

Lys Leu Leu Thr Phe Glu Lys Val Glu Glu Met Val Lys Lys Arg Val
        195                 200                 205

Gln Lys Lys Ala Glu Thr Phe Gly Gln Glu Val Lys Phe Asn Ser Gly
        210                 215                 220
```

-continued

```
Tyr Gly Asp Glu Ser Lys Lys Tyr Lys Val Asp Pro Leu Leu Ala
225                 230             235             240

Ser Arg Ile Tyr Gly Glu Trp Leu Ile Pro Leu Thr Lys Leu Val Glu
                245             250             255

Val Glu Tyr Leu Leu Arg Arg Leu Asp
            260             265
```